(12) United States Patent
Furukawa et al.

(10) Patent No.: US 8,507,504 B2
(45) Date of Patent: Aug. 13, 2013

(54) PROCESS FOR PRODUCING BICYCLOANILINE DERIVATIVES

(75) Inventors: Shuntaro Furukawa, Mito (JP); Taketo Ikeno, Niigata (JP); Shinji Kato, Nagoya (JP); Masashi Kawasaki, Osaka (JP); Hisaki Kojima, Nagoya (JP); Wataru Minagawa, Saitama (JP); Naotaka Sawada, Ibaraki (JP); Fuyuki Yamamoto, Tsukuba (JP); Sachin Lohani, Annandale, NJ (US); Yaling Wang, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 136 days.

(21) Appl. No.: 12/996,801

(22) PCT Filed: Jun. 2, 2009

(86) PCT No.: PCT/US2009/045917
§ 371 (c)(1),
(2), (4) Date: Dec. 8, 2010

(87) PCT Pub. No.: WO2009/151997
PCT Pub. Date: Dec. 17, 2009

(65) Prior Publication Data
US 2011/0092520 A1    Apr. 21, 2011

Related U.S. Application Data

(60) Provisional application No. 61/131,781, filed on Jun. 12, 2008.

(51) Int. Cl.
*C07D 487/00*    (2006.01)
*A61K 31/505*    (2006.01)

(52) U.S. Cl.
USPC .................. 514/262.1; 544/256; 546/143

(58) Field of Classification Search
USPC .................. 544/256; 546/143; 514/262.1
See application file for complete search history.

(56) References Cited

U.S. PATENT DOCUMENTS

| 6,596,734 B1 | 7/2003 | Feller et al. |
| 6,800,268 B2 | 10/2004 | Uchino et al. |
| 2004/0044012 A1 | 3/2004 | Dobrusin et al. |
| 2005/0261313 A1 | 11/2005 | Askew et al. |

FOREIGN PATENT DOCUMENTS

| EP | 2168966 A1 | 3/2010 |
| WO | 2007126122 A1 | 11/2007 |
| WO | 2008153207 A1 | 12/2008 |

*Primary Examiner* — Bruck Kifle
(74) *Attorney, Agent, or Firm* — John E. Switzer; David A. Muthard

(57) ABSTRACT

The present invention relates to a process for producing a hydrate of 3-(2,6-dichlorophenyl)-4-imino-7-[(2'-methyl-2',3'-dihydro-1'H-spiro[cyclopropane-1,4'-isoquinolin]-7'-yl) amino]-3,4-dihydropyrimido[4,5-d]pyrimidin-2(1H)-one (Compound A) or of a pharmaceutically acceptable salt of Compound A and a crystalline form of Compound A or of a pharmaceutically acceptable salt of Compound A, which are useful in the field of treatment of various cancers as a kinase inhibitor, especially as a Wee1 kinase inhibitor.

10 Claims, 1 Drawing Sheet

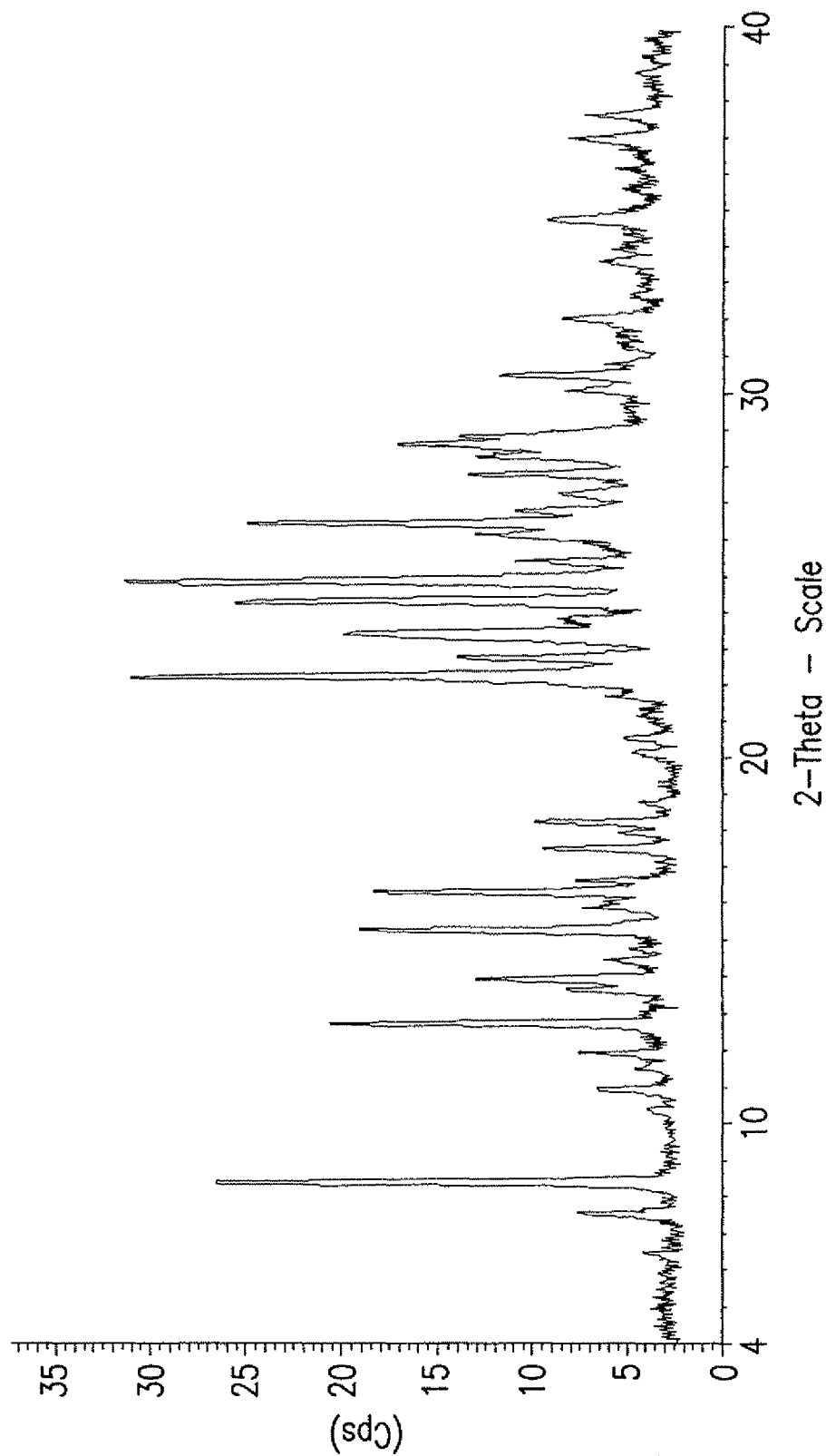

PROCESS FOR PRODUCING BICYCLOANILINE DERIVATIVES

TECHNICAL FIELD

The present invention is useful in the field of medicine. More precisely, the present invention relates to a process for producing a hydrate of 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one (Compound A) or of a pharmaceutically acceptable salt of Compound A and a crystalline form of Compound A or of a pharmaceutically acceptable salt of Compound A, which are useful in the field of treatment of various cancers as a kinase inhibitor, especially as a Wee1 kinase inhibitor, and also relates to a novel intermediate necessary for producing the same and a process for producing the same.

BACKGROUND ART

Cells have a checkpoint mechanism such that, when the DNA therein is damaged, then the cells temporarily stop the cell cycle and repair the damaged DNA (*Cell Proliferation*, Vol. 33, pp. 261-274). In about a half of human cancers, a cancer-suppressor gene, p53 is mutated or depleted and thereby the cells have lost the G1 checkpoint function thereof. However, such cancer cells still keep the G2 checkpoint function remaining therein, which is considered to be one factor of lowering the sensitivity of the cells to DNA-active anticancer agents and to radiations.

A Wee1 kinase is a tyrosine kinase that participates in the G2 checkpoint of a cell cycle. Wee1 phosphorylates Cdc2 (Cdk1) tyrosine 15 that participates in the progress to the M stage from the G2 stage in a cell cycle, thereby inactivating Cdc2 and temporarily stopping the cell cycle at the G2 stage (*The EMBO Journal*, Vol. 12, pp. 75-85). Accordingly, in cancer cells having lost the p53 function therein, it is considered that the G2 checkpoint function by Wee1 is important for repairing the damaged DNA so as to evade the cell death. Heretofore, it has been reported that the Wee1 expression reduction by RNA interference or the Wee1 inhibition by compounds may increase the sensitivity of cancer cells to adriamycin, X ray or gamma ray (*Cancer Biology & Therapy*, Vol. 3, pp. 305-313; *Cancer Research*, Vol. 61, pp. 8211-8217). From the above, it is considered that a Wee1 inhibitor may inhibit the G2 checkpoint function of p53-depleted cancer cells, thereby enhancing the sensitivity of the cells to DNA-active anticancer agents and to radiations.

As a low-molecular Wee1 kinase inhibitor, for example, known are compounds described in US Application 2005/0250836, WO2003/091255, *Cancer Research*, Vol. 61, pp. 8211-8217, or *Bioorg & Med. Chem. Lett.*, Vol. 15, pp. 1931-1935. However, the compounds described in these references quite differ from the compounds of the invention in terms of their structures.

On the other hand, Japanese patent application No. 2007-159217 (filed on Jun. 15, 2007) discloses dihydrochloride of Compound A per se and a certain solid form thereof, which have an excellent Wee1 kinase-inhibitory effect and are useful in the field of the treatment of cancer.

BRIEF DESCRIPTION OF THE DRAWINGS

FIG. 1 is the XRPD pattern for a crystalline form of a 3.5 hydrate of dihydrochloride of Compound A.

DISCLOSURE OF INVENTION

The invention provides a novel hydrate of Compound A or hydrate of a pharmaceutically acceptable salt of Compound A of formula (I):

Compound A

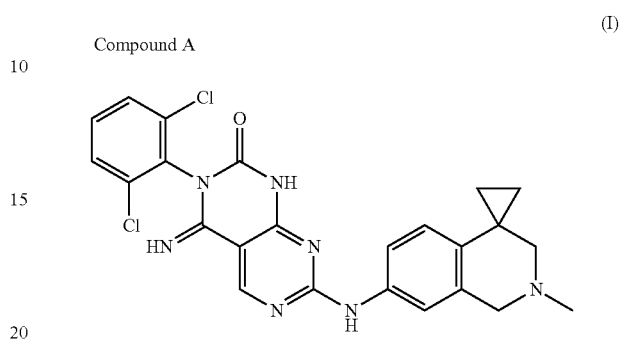

(I)

and a crystalline form of Compound A or of a pharmaceutically acceptable salt of Compound A.

The novel hydrate of Compound A or hydrate of a pharmaceutically acceptable salt of Compound A and a crystalline form of Compound A or of a pharmaceutically acceptable salt of Compound A, can be provided stably and constantly from the standpoint of the manufacturing process, and they are useful in the field of the treatment of cancer.

The novel hydrate of Compound A or hydrate of a pharmaceutically acceptable salt of Compound A and a crystalline faun of Compound A or of a pharmaceutically acceptable salt of Compound A, as well as Compound A per se or a pharmaceutically acceptable salt thereof, have a kinase-inhibitory effect, especially a Wee1 kinase-inhibitory effect, and are therefore useful as pharmaceutical agents for the treatment of various cancers such as brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma.

In particular, the novel crystalline forms of a hydrate of a pharmaceutically acceptable salt of Compound A, as well as Compound A per se or a pharmaceutically acceptable salt thereof, are useful as pharmaceutical agents, for example, for the treatment of breast cancer, lung cancer, pancreatic cancer, colon cancer, ovarian cancer, acute leukemia, chronic lymphatic leukemia, chronic myelocytic leukemia, Hodgkin's lymphoma.

The term "Compound A" as referred to herein means a compound of the above-described chemical structural formula and includes any amorphous form, polymorphic crystalline forms, hydrate, solvate and the mixture thereof.

That is, the present invention relates to the following inventions.

(1) A hydrate of Compound A or a hydrate of a pharmaceutically acceptable salt of Compound A of formula (I):

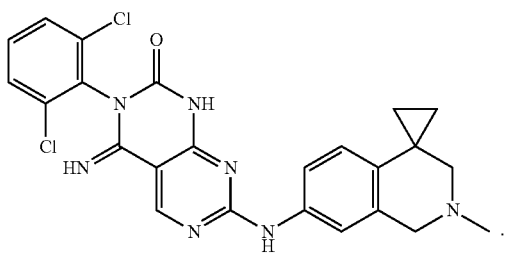

(2) A hydrate of dihydrochloride of Compound A of formula (I).

(3) A crystalline form of a hydrate of Compound A of formula (I) or of a hydrate of a pharmaceutically acceptable salt of Compound A of formula (I).

(4) A crystalline form of a hydrate of dihydrochloride of Compound A of formula (I).

(5) The crystalline form according to the above (4), wherein the hydrate is a 3.5 hydrate.

(6) The crystalline form according to the above (5), which has an X-ray powder diffraction pattern, obtained using Cu K alpha radiation, containing the following angle 2 theta values: 8.4°, 22.3° and 24.9°, and at least one angle 2 theta value selected from the group consisting of: 12.7°, 15.3°, 16.3°, 24.4°, 26.5° and 28.6°.

(7) A process for preparing a crystalline form of a 3.5 hydrate of dihydrochloride of Compound A of formula (I), which comprises the steps of:

(a) concentrating a solution of Compound A in an organic solvent to form slurry;

(b) treating the slurry of step (a) with hydrogen chloride in a solvent on heating;

(c) cooling the slurry of step (b) to room temperature;

(d) collecting crystals from the resulting slurry of step (c);

(e) drying the crystals of step (d); and (f) treating the dried crystals of step (e) with wet inert gas to stabilize water content in the desired crystalline form.

(8) A crystalline form of dihydrochloride of Compound A of formula (I), which is prepared by the process according to the above (7).

(9) A pharmaceutical composition comprising a therapeutically-effective amount of the compound according to any one of above (1)-(6) or (8), and pharmaceutically acceptable carrier or diluent.

The present invention also relates to a novel intermediate necessary for producing the above compound and a process for producing the intermediate. That is, the present invention also relates to the following invention.

(10) A process for preparing a compound of formula (6):

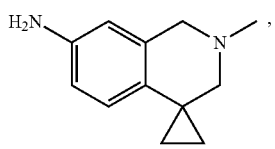

or a salt thereof, which comprises the steps of
(a) reacting a compound of formula (1):

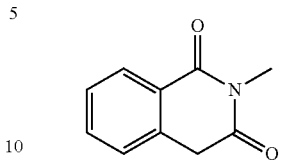

with a compound of formula (2):

$$X^1—CH_2CH_2—X^2 \quad (2)$$

wherein $X^1$ and $X^2$ each independently is a leaving group, to obtain a compound of formula (3):

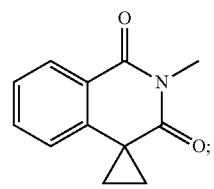

(b) nitrating a compound of formula (3) to obtain a compound of formula (4):

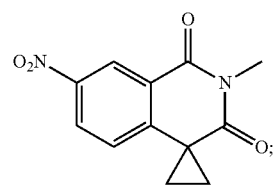

(c) reducing oxo groups of the compound of formula (4) to obtain a compound of formula (5):

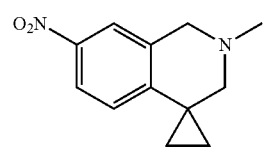

or a salt thereof;

(d) reducing a nitro group of the compound of formula (5) or a salt thereof to obtain a compound of formula (6) or a salt thereof; and optionally converting said compound of formula (6) into a salt thereof.

In one aspect, the crystalline form of a 3.5 hydrate of dihydrochloride of Compound A is identified by an X-ray powder diffraction pattern, obtained using Cu K alpha radiation, containing the following angle 2 theta values: 8.4°, 22.3° and 24.9°.

In another aspect, the crystalline form of a 3.5 hydrate of dihydrochloride of Compound A is identified by an X-ray powder diffraction pattern, obtained using Cu K alpha radiation, containing the following angle 2 theta values: 8.4°, 22.3° and 24.9°, and at least one angle 2 theta value selected from the group consisting of: 12.7°, 15.3°, 16.3°, 24.4°, 26.5° and 28.6°.

In another aspect, the crystalline form of a 3.5 hydrate of dihydrochloride of Compound A is identified by an X-ray powder diffraction pattern, obtained using Cu K alpha radiation, containing the following angle 2 theta values: 8.4°, 22.3°, 24.9° and 12.7°.

The numerical analysis to identify the various forms of the invention should be made objectively by considering that the values may include some experimental error depending on the measuring conditions. Therefore, the invention includes any forms substantially identified by the above-mentioned values for the identification.

In one aspect, the invention provides a process for preparing a crystalline form of a 3.5 hydrate of dihydrochloride of Compound A, which comprises the steps of:
(a) concentrating a solution of Compound A in an organic solvent to form slurry;
(b) treating the slurry of step (a) with hydrogen chloride in a solvent on heating;
(c) cooling the slurry of step (b) to room temperature;
(d) collecting crystals from the resulting slurry of step (c);
(e) drying the crystals of step (d); and
(f) treating the dried crystals of step (e) with wet inert gas to stabilize water content in the desired crystalline form.

In one embodiment, the solution of Compound A in an organic solvent is a solution of a free base of Compound A and said organic solvent is an alcohol-containing solvent.

In another embodiment, alcohol for the alcohol-containing solvent is selected from: methanol, ethanol, propanol, isopropanol etc. and a mixture thereof, preferably methanol and ethanol.

In yet another embodiment, the alcohol-containing solvent may contain organic or inorganic solvents other than alcohol, such as chloroform, dichloromethane, N,N-dimethylformamide, and water.

In one embodiment, the solution of a free base of Compound A is prepared by treating a suspension of dihydrochloride of Compound A in an organic solvent such as chloroform, methanol and a mixture thereof, with a base, preferably aqueous inorganic base solution including sodium hydrogencarbonate, sodium carbonate, potassium carbonate, cesium carbonate, sodium hydroxide, potassium hydroxide, and a mixture thereof, and then separating an organic layer including the free base of Compound A.

In another embodiment, said aqueous inorganic base solution includes aqueous sodium hydrogencarbonate solution which concentration may be 1-10%, preferably 3-8%.

In yet another embodiment, excessive molar amount of the base is used relative to one mol of dihydrochloride of Compound A.

In one embodiment, hydrogen chloride in a solvent of step (b) is hydrogen chloride in organic or inorganic solvents such as alcohol, preferably methanol or ethanol, and water, more preferably ethanol.

In one embodiment, crystals of a 3.5 hydrate of dihydrochloride of Compound A are added to the slurry of step (b) after treatment with hydrogen chloride as seed crystals.

In one embodiment, the step (b) is conducted on heating at 45-65° C., preferably at 50-60° C.

In another embodiment, the resulting slurry of step (b) may be aged for over 0.5 hour, preferably about 1 hour at the same temperature of step (b).

In one embodiment, the room temperature of step (c) is 10-40° C., preferably 20-30° C.

In another embodiment, the resulting slurry of step (c) may be aged for over 0.5 hour, preferably 1-24 hours, more preferably overnight id est 8-16 hours at room temperature.

In one embodiment, the collecting crystals of step (d) are conducted by filtration.

In one embodiment, the drying of step (e) is conducted under inert gas flow, such as helium, argon, nitrogen, and a mixture thereof, preferably nitrogen gas flow, for several hours and then under reduced pressure over 0.5 hour, preferably 1-24 hours, more preferably overnight id est 8-16 hours at room temperature id est 10-40° C., preferably 20-30° C.

In one embodiment, the inert gas of step (f) includes, but is not limited to, helium, argon, nitrogen, and a mixture thereof, preferably nitrogen gas.

In one embodiment, the step (1) is conducted at room temperature id est 10-40° C., preferably 20-30° C.

In one embodiment, relative humidity of the wet inert gas of step (f) is from about 5% to less than 100%.

In another embodiment, relative humidity of the wet inert gas of step (f) is from 30% to 60%.

In another aspect, the invention provides a crystalline form of dihydrochloride of Compound A, which is prepared by the above process.

In an embodiment, the process for preparing the above intermediate will be illustrated in detail below.

The step (a) of producing a compound of formula (3), by reacting a compound of formula (1) with a compound of formula (2) can be conducted in such a way that the compound (1) is reacted with a compound of formula (2) of about 1 mol to an excessive molar amount, preferably from 1 to 5 cools, relative to 1 mol of the compound (1), in an inert solvent at about −20° C. to 80° C., preferably 40° C. to 80° C. for about 1 to 120 hours, preferably about 1 to 20 hours.

The leaving group for $X^1$ or $X^2$ includes, for example, a halogen atom such as a fluorine atom, a chlorine atom, a bromine atom or an iodine atom; a methylsulfinyl group; an organic sulfonyl group such as a methylsulfonyl group, an ethylsulfonyl group, a phenylsulfonyl group; and an organic sulfonyloxy group such as a methylsulfonyloxy group, a trifluoromethylsulfonyloxy group, a p-tolylsulfonyloxy group; and of those, preferred is a bromine atom.

Examples of the inert solvent which may be used in the above step (a) include tetrahydrofuran, diethyl ether, tert-butyl methyl ether, diisopropyl ether, dibutyl ether, methanol, ethanol, isopropanol, propanol, acetone, ethyl acetate, isopropyl acetate and cyclopentyl methyl ether, dimethylformamide, dimethyl sulfoxide or a mixed solvent thereof, among which dimethylformamide, tetrahydrofuran, cyclopentyl methyl ether or tert-butyl methyl ether is preferable.

Preferably, the reaction is attained in the presence of a base and phase transfer catalyst.

The phase transfer catalyst includes, for example, tetrabutylammonium hydrogensulfate, tetrabutylammonium chloride, tetrabutylammonium bromide, tetrabutylammonium iodide, dodecyltrimethylammonium chloride, hexadecyltrimethylammonium chloride, benzylcetyldimethylammonium chloride, benzyldimethylphenylammonium chloride, benzyltributylammonium chloride, benzyltriethylammonium chloride, decyltrimethylammonium chloride, octyltrimethylammonium chloride, phenyltrimethylammonium chloride, tetramethylammonium chloride, tetraethylammonium chloride, trioctylmethylammonium chloride, benzyltriethylammonium hydroxide, benzyltrimethylammonium hydroxide, hexadecyltrimethylammonium hydroxide, phenyltrimethylammonium hydroxide, tetrabutylammonium hydroxide, benzyltrimethylammonium bromide, benzyltriethylammonium bromide, benzyltributylammonium bromide, decyltrimethylammonium bromide, didecyldimethylammonium bromide, dilauryldimethylammonium bromide, hexadecyltrimethylammonium bromide, octyltrimethylammonium bromide, phenyltrimethylammonium bromide, tetradecylammonium bromide, tetrahexylammonium bromide, tetrapropylammonium bromide, benzyltriethylammonium iodide, ethyltripropylammonium iodide, tetraethylammonium iodide, tetrahexylammonium iodide, tetrapropylammonium iodide, and tetrabutylammonium hydrogensulfate is preferable.

The amount of the phase transfer catalyst to be used may be generally from 0.01 to excessive molar amount, preferably from 0.02 to 1.5 mols relative to one mol of the compound of formula (1).

The base includes, for example, organic bases such as triethylamine, diisopropylethylamine, pyridine, 4-dimethylaminopyridine; and inorganic bases such as sodium hydrogencarbonate, sodium carbonate, potassium carbonate, cesium carbonate, sodium hydroxide, potassium hydroxide.

The amount of the base to be used may be generally from an equimolar amount to an excessive molar amount, preferably from 1 to 3 mols relative to one mol of the compound of formula (1).

The step (b) of producing a compound of formula (4), by nitrating a compound of formula (3) can be conducted in such a way that the compound (3) is reacted with a nitration agent of about 0.5 mols to an excessive molar amount, preferably from 1 to 5 mols, relative to 1 mol of the compound (3), in an inert solvent at about $-20°$ C. to $80°$ C., preferably $-5°$ C. to $5°$ C. for about 1 to 120 hours, preferably about 1 to 10 hours.

Examples of the nitration agent which may be used in the above step (b) include nitric acid, finning nitric acid, copper nitrate, sodium nitrate, potassium nitrate, ammonium nitrate, nitronium tetrafluoroborate, nitrogen dioxide, among which nitric acid is preferable.

Examples of the inert solvent which may be used in the above step (b) include tetrahydrofuran, diethyl ether, tert-butyl methyl ether, diisopropyl ether, dibutyl ether, methanol, ethanol, isopropanol, propanol, acetone, ethyl acetate, isopropyl acetate, water, acetic acid, acetic anhydride, chloroform, dichloromethane and cyclopentyl methyl ether, or a mixed solvent thereof, among which water, acetic acid is preferable.

The step (c) of producing a compound of formula (5) or a salt thereof, by reducing oxo groups of the compound of formula (4) can be conducted in such a way that the compound (4) is reacted with a reducing agent of about 0.5 mols to an excessive molar amount, preferably from 1 to 5 mols, relative to 1 mol of the compound (4), in an inert solvent at about $-20°$ C. to $80°$ C., preferably $50°$ C. to $70°$ C. for about 1 to 120 hours, preferably about 5 to 60 hours.

Examples of the reducing agent which may be used in the above step (c) include borane-dimethylsulfide, borane-tetrahydrofuran, borane-N,N-diethylaniline, and sodium borohydride with acid, such as boron-trifluoride diethyletherate or sulfuric acid, among which borane-dimethylsulfide or borane-tetrahydrofuran is preferable.

Examples of the inert solvent which may be used in the above step (c) include tetrahydrofuran, diethyl ether, tert-butyl methyl ether, diisopropyl ether, dibutyl ether, methanol, ethanol, isopropanol, propanol, acetone, ethyl acetate, isopropyl acetate and cyclopentyl methyl ether, or a mixed solvent thereof, among which tetrahydrofuran, cyclopentyl methyl ether or tert-butyl methyl ether is preferable.

The step (d) of producing a compound of formula (6) or a salt thereof, by reducing a nitro group of the compound of formula (5) or a salt thereof can be conducted in such a way that the compound (5) or a salt thereof is reacted with a reducing agent of about 0.5 mols to an excessive molar amount, preferably from 1 to 5 mols, relative to 1 mol of the compound (5) or a salt thereof, in an inert solvent at about $-20°$ C. to $80°$ C., preferably $20°$ C. to $80°$ C. for about 0.5 to 120 hours, preferably about 0.5 to 3 hours.

In case where the compound of formula (6) is a free base, then this may be converted into a salt thereof, by treating the said compound (6) with an inorganic acid or organic acid in an ordinary manner; and on the contrary, in case where the compound of formula (6) is a salt form, the salt may also be converted into a free compound in an ordinary manner.

Examples of the reducing agent which may be used in the above step (d) include zinc, iron, fin(II) chloride, tin, sodium sulfide, formic acid, ammonium formate, hydrogen, and hydrazine among which zinc or iron is preferable.

Examples of the inert solvent which may be used in the above step (d) include tetrahydrofuran, diethyl ether, tert-butyl methyl ether, diisopropyl ether, dibutyl ether, methanol, ethanol, isopropanol, propanol, acetone, ethyl acetate, isopropyl acetate and cyclopentyl methyl ether, or a mixed solvent thereof, among which ethanol or isopropyl alcohol is preferable.

The "salt" of the compound of formula (5) or (6) mean ordinary salt used in the field of organic chemistry, for example, acid-addition salt.

The acid-addition salt include, for example, an inorganic acid salt such as hydrochloride, sulfate, nitrate, phosphate, perchlorate; an organic acid salt such as maleate, fumarate, tartrate, citrate, ascorbate, trifluoroacetate, methanesulfonate, isethionate, benzenesulfonate, p-toluenesulfonate, preferably hydrochloride. A dihydrochloride is more preferred for the compound of formula (6).

The compound of formula (1) and (2) may be commercially available, or may be produced according to known methods or according to methods similar to them, or according to the methods described below, or according to the methods described in Examples and Production Examples, optionally as suitably combined.

The pharmaceutical test examples for Compound A are shown below.

Pharmacological Test 1 (Weel Kinase-Inhibitory Effect)
(1) Purification of Weel Kinase:

A cDNA of Weel kinase with glutathion-5-transferase (GST) fused at the amino terminal thereof was inserted into a baculovirus expression vector to construct a recombinant baculovirus, with which cells of an insect cell line Sf9 were infected for high expression therein. The infected cells were recovered and solubilized, and then the GST-tagged Weel kinase protein was adsorbed by a glutathion column, and eluted from the column with glutathion, and the active fraction was desalted in a desalting column to give a purified enzyme.

(2) Determination of Weel Kinase Activity:

In determination of the Weel kinase activity, a synthetic peptide, Poly(Lys,Tyr) Hydrobromide (Lys:Tyr (4:1)) bought from Sigma was used as the substrate.

The amount of the reaction liquid was 21.1 μL; and the composition of the reaction buffer was 50 mM Tris-HCl buffer (pH 7.4)/10 mM magnesium chloride/1 mM dithiothreitol. The purified Weel kinase, 2.5 μg of the substrate peptide, 10 μM of non-labeled adenosine triphosphate (ATP) and 1 μCi of [$\gamma$-$^{33}$P]-labeled ATP (2500 Ci/mmol or more) were added to it, and reacted at $30°$ C. for 30 minutes. Next, 10 μL of 350 mM phosphate buffer was added to the reaction system to stop the reaction. The substrate peptide was adsorbed by a P81 paper filter 96-well plate, then washed a few times with 130 mM phosphate buffer, and its radioactivity was counted with a liquid scintillation counter. The [$\gamma$-$^{33}$P]-labeled ATP was bought from Amersham Bioscience.

To add the test compound to the reaction system, the compound was diluted with dimethylsulfoxide (DMSO) to prepare a series of dilutions. 1.1 µL of each dilution was added to the reaction system. As a control, 1.1 µL of DMSO was added to the reaction system.

As a result, the half maximal inhibitory concentration ($IC_{50}$) value of dihydrochloride of Compound A obtained in Reference Example 2 was 5 nM.

Pharmacological Test 2 (Tumor Growth Inhibitory Effect)

Human colon cancer cells WiDr (obtained from ATCC) were implanted into the subcutaneous area of the back of F344/N Jcl-rnu nude rats. 12 days after the implantation, 5 mg/kg of gemcitabine (Gemzar, from Eli Lily) was intravenously administered to them; and after 24 hours, a test compound suspended in a solvent (0.5% methyl cellulose) was orally administered thereto. This was repeated once a week for 3 weeks. The tumor volume (0.5×major diameter×(minor diameter)$^2$) was measured on days 0, 3, 6, 10, 13, 17, 20, 24 and 27 (the first gemcitabine administration is on day 0). The relative tumor volume was calculated, based on the tumor volume on day 0, as 1. The tumor growth rate (% T/C) was obtained according to the formulae mentioned below.

In case where the tumor volume change from day 0 in the test compound administration group is more than 0 (>0):

% T/C=(tumor volume change in the test compound group on days 3, 6, 10, 13, 17, 20, 24 and 27/tumor volume change in the control group on days 3, 6, 10, 13, 17, 20, 24 and 27)×100.

In case where the tumor volume change from day 0 in the test compound administration group is less than 0 (<0):

% T/C=(tumor volume change in the test compound group on days 3, 6, 10, 13, 17, 20, 24 and 27/tumor volume change in the test compound group on day 0)×100.

The data of the tumor growth inhibitory effect are shown in Table 1.

TABLE 1

| Compound | n | day 3 | day 6 | day 10 | day 13 | day 17 | day 20 | day 24 | day 27 |
|---|---|---|---|---|---|---|---|---|---|
| | | | | | % T/C | | | | |
| Control | 5 | 100 | 100 | 100 | 100 | 100 | 100 | 100 | 100 |
| Gemcitabine 5 mg/kg | 5 | 62 | 67 | 66 | 64 | 57 | 49 | 52 | 54 |
| Gemcitabine + Test compound*1 15 mg/kg | 5 | −16 | −6 | −17 | −13 | −17 | −5 | 7 | 13 |
| Test compound*1 15 mg/kg | 5 | 107 | 100 | 87 | 91 | 88 | 85 | 83 | 88 |

Test compound*[1] was obtained in Reference Example 2.
Gemcitabine was administered on days 0, 7 and 14.
Test compound*[1] was administered on days 1, 8 and 15.

The gemcitabine administration reduced the tumor growth rate; and, the combined administration of the compound of the invention and gemcitabine further reduced the tumor growth rate. In the group given high-dose combined administration, tumor involution was observed.

As mentioned above, when combined with any other anticancer agent, the compound of the invention enhanced the anticancer effect of the other anticancer agent.

The novel hydrate of Compound A or hydrate of a pharmaceutically acceptable salt of Compound A and a crystalline form of Compound A or of a pharmaceutically acceptable salt of Compound A, as well as Compound A per se or a pharmaceutically acceptable salt thereof, can be administered orally or parenterally, and after formulated into preparations suitable to such administration modes, the compounds can be used as pharmaceutical compositions or anticancer agents.

The term "cancer" as referred to in this description includes various sarcoma and carcinoma and includes solid cancer and hematopoietic cancer. The solid cancer as referred to herein includes, for example, brain tumor, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' tumor, skin cancer, malignant melanoma, neuroblastoma, osteosarcoma, Ewing's tumor, soft part sarcoma. On the other hand, the hematopoietic cancer includes, for example, acute leukemia, chronic lymphatic leukemia, chronic myelocytic leukemia, polycythemia vera, malignant lymphoma, multiple myeloma, Hodgkin's lymphoma, non-Hodgkin's lymphoma.

The term "treatment of cancer" as referred to in this description means that an anticancer agent is administered to a cancer case so as to inhibit the growth of the cancer cells in the case. Preferably, the treatment results in cancer growth regression, or that is, it reduces the size of a detectable cancer. More preferably, the treatment results in complete disappearance of cancer.

The novel hydrate of Compound A or hydrate of a pharmaceutically acceptable salt of Compound A and a crystalline form of Compound A or of a pharmaceutically acceptable salt of Compound A, as well as Compound A per se or a pharmaceutically acceptable salt thereof, are expected to be effective especially for human solid cancer. The human solid cancer includes, for example, brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma.

The pharmaceutical composition or anticancer agent of the invention may contain a pharmaceutically acceptable carrier or diluent. Here, the "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.);

additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

With regard to each preparation of the pharmaceutical composition or anticancer agent of the invention, various preparation forms can be selected, and examples thereof include oral preparations such as tablets, capsules, powders, granules or liquids, or sterilized liquid parenteral preparations such as solutions or suspensions, suppositories, ointments and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the compound of the above Formula (I) as an active ingredient, based on the total weight of the preparation.

Liquid preparations are produced in the forms of suspension, syrup, injection and drip infusion (intravenous fluid) using appropriate additives that are conventionally used in liquid preparations, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of the preparation.

Liquid preparations such as suspension or syrup for oral administration may contain, for example, 0.1 to 10% by weight of an active ingredient based on the total weight of the preparation.

The preparation can be prepared by a person having ordinary skill in the art according to conventional methods or common techniques. For example, a preparation can be carried out, if the preparation is an oral preparation, for example, by mixing an appropriate amount of the compound of the invention with an appropriate amount of lactose and filling this mixture into hard gelatin capsules which are suitable for oral administration. On the other hand, preparation can be carried out, if the preparation containing the compound of the invention is an injection, for example, by mixing an appropriate amount of the compound of the invention with an appropriate amount of 0.9% physiological saline and filling this mixture in vials for injection.

The novel hydrate of Compound A or hydrate of a pharmaceutically acceptable salt of Compound A and a crystalline form of Compound A or of a pharmaceutically acceptable salt of Compound A, as well as Compound A per se or a pharmaceutically acceptable salt thereof, may be used, optionally in combination with any other agent useful for the treatment of various cancers or with radiotherapy. The individual ingredients for such combination may be administered at different times or at the same time as divided preparations or one preparation during the term of treatment. Accordingly, the invention should be so interpreted that it includes all modes of administration at the same time or at different times, and the administration in this invention should be interpreted so. The scope of the combination of the compound of the invention and any other agent useful for the above-mentioned diseases should include, in principle, any and all combinations thereof with any and all pharmaceutical agents useful for the treatment of the above-mentioned diseases.

Radiation therapy itself means an ordinary method in the field of treatment of cancer. For radiation therapy, various radiations such as X-ray, $\gamma$-ray, neutron ray, electron beam and proton beam; and radiation sources, can be used. In a most popular radiation therapy, a linear accelerator is used for irradiation with external radiations, $\gamma$-ray.

The novel hydrate of Compound A or hydrate of a pharmaceutically acceptable salt of Compound A and a crystalline form of Compound A or of a pharmaceutically acceptable salt of Compound A, as well as Compound A per se or a pharmaceutically acceptable salt thereof, may be combined with a radiation therapy to enhance the therapeutical effect in radiation therapy; and therefore they may be useful as a radiation sensitizer in the field of treatment of cancer.

Another aspect of the novel hydrate of Compound A or hydrate of a pharmaceutically acceptable salt of Compound A and a crystalline form of Compound A or of a pharmaceutically acceptable salt of Compound A, as well as Compound A per se or a pharmaceutically acceptable salt thereof, is that the compounds are also useful as a sensitizer for any other anticancer agents in the field of treatment of cancer.

The novel hydrate of Compound A or hydrate of a pharmaceutically acceptable salt of Compound A and a crystalline form of Compound A or of a pharmaceutically acceptable salt of Compound A, as well as Compound A per se or a pharmaceutically acceptable salt thereof, may be combined with radiation therapy and/or combined with chemotherapy using any other anticancer agents described below in their use for treatment of cancer.

"Sensitizer" for radiation therapy or anticancer agent as referred to herein is meant to indicate a medical agent which, when used as combined with radiation therapy and/or chemotherapy with an anticancer agent, may additively or synergistically augment the therapeutical effect of that radiation therapy and/or chemotherapy.

The agents to be in the combined preparations in the invention may have any forms selected in any manner, and they may be produced in the same manner as that for the above-mentioned preparations. The combined agent comprising the compound of the invention and some other anticancer agent may be readily produced by a person skilled in the art according to ordinary methods or conventional techniques.

The above-mentioned combination includes not only the compositions of the invention that further contain one other active ingredient but also those further containing two or more other active substances. There are a lot of examples of the combination of the composition of the invention and one or two or more active substances selected from the pharmaceutical agents for the above-mentioned diseases.

The agents to be combined with the compositions include, for example, an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, interferons, biological response modifiers and other anticancer agents as well as pharmaceutically acceptable salt(s) or ester(s) thereof.

The term "anticancer alkylating agent" as used in the present specification refers to an alkylating agent having anticancer activity, and the term "alkylating agent" herein generally refers to an agent giving an alkyl group in the alkylation reaction in which a hydrogen atom of an organic compound is substituted with an alkyl group. The term "anticancer alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "anticancer antimetabolite" as used in the specification refers to an antimetabolite having anticancer activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "anticancer antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are cytarabine, gemcitabine and the like.

The term "anticancer antibiotic" as used in the specification refers to an antibiotic having anticancer activity, and the "antibiotic" herein includes substances that are produced by microorganisms and inhibit cell growth and other functions of microorganisms and of other living organisms. The term "anticancer antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin, and preferred are doxorubicin, mitomycin C and the like.

The term "plant-derived anticancer agent" as used in the specification includes compounds having anticancer activities which originate from plants, or compounds prepared by applying chemical modification to the foregoing compounds. The term "plant-derived anticancer agent" may be exemplified by vincristine, vinblastine, vindesine, etoposide, sobuzoxane, docetaxel, paclitaxel and vinorelbine, and preferred are etoposide and the like.

The term "anticancer camptothecin derivative" as used in the specification refers to compounds that are structurally related to camptothecin and inhibit cancer cell growth, including camptothecin per se. The term "anticancer camptothecin derivative" is not particularly limited to, but may be exemplified by, camptothecin, 10-hydroxycamptothecin, topotecan, irinotecan or 9-aminocamptothecin, with camptothecin being preferred. Further, irinotecan is metabolized in vivo and exhibits anticancer effect as SN-38. The action mechanism and the activity of the camptothecin derivatives are believed to be virtually the same as those of camptothecin (e.g., Nitta, et al., *Gan to Kagaku Ryoho*, 14, 850-857 (1987)).

The term "anticancer platinum coordination compound" as used in the specification refers to a platinum coordination compound having anticancer activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato)platinum (II); ethylenediaminemalonatoplatinum (II); aqua(1,2-diaminodicyclohexane)sulfatoplatinum (II); aqua (1,2-diaminodicyclohexane)malonatoplatinum (II); (1,2-diaminocyclohexane)malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is cisplatin. Further, other anticancer platinum coordination compounds mentioned in the specification are known and are commercially available and/or producible by a person having ordinary skill in the art by conventional techniques.

The term "anticancer tyrosine kinase inhibitor" as used in the specification refers to a tyrosine kinase inhibitor having anticancer activity, and the term "tyrosine kinase inhibitor" herein refers to a chemical substance inhibiting "tyrosine kinase" which transfers a γ-phosphate group of ATP to a hydroxyl group of a specific tyrosine in protein. The term "anticancer tyrosine kinase inhibitor" may be exemplified by gefitinib, imatinib or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having anticancer activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon α, interferon α-2a, interferon α-2b, interferon β, interferon γ-1a and interferon γ-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofuran, picibanil and ubenimex.

The term "other anticancer agent" as used in the specification refers to an anticancer agent which does not belong to any of the above-described agents having anticancer activities. Examples of the "other anticancer agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diffitox, aldesleukin, thyrotropin alfa, arsenic trioxide, bortezomib, capecitabine, and goserelin.

The above-described terms "anticancer alkylating agent", "anticancer antimetabolite", "anticancer antibiotic", "plant-derived anticancer agent", "anticancer platinum coordination compound", "anticancer camptothecin derivative", "anticancer tyrosine kinase inhibitor", "monoclonal antibody", "interferon", "biological response modifier" and "other anticancer agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned anticancer alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from GlaxoSmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned anticancer antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned anticancer antibiotics are commercially available, as exemplified by the following: actinomycin D from Banyu Pharmaceutical Co., Ltd. as Cosmegen (tradename); doxorubicin from Kyowa Hakko Kogyo Co., Ltd. as adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived anticancer agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tradename); paclitaxel from Bristol-Myers Squibb Co. as Taxol (tradename); and vinorelbine from Kyowa Hakko Kogyo Co., Ltd. as Navelbine (tradename).

The above-mentioned anticancer platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned anticancer camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned anticancer tyrosine kinase inhibitors are commercially available, as exemplified by the following: gefitinib from AstraZeneca Corp. as Iressa (tradename); imatinib from Novartis AG as Gleevec (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename). The above-mentioned interferons are commercially available, as exemplified by the following: interferon α from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon 3 from Mochida Pharmaceutical Co., Ltd. as IFNβ (tradename); interferon γ-1a from Shionogi & Co., Ltd. as Immunomax-γ (tradename); and interferon γ-n1 from Otsuka Pharmaceutical Co., Ltd. as ° gamma (tradename).

The above-mentioned biological response modifiers are commercially available, as exemplified by the following: krestin from Sankyo Co., Ltd. as krestin (tradename); lentinan from Aventis Corp. as Lentinan (tradename); sizofuran from Kaken Seiyaku Co., Ltd. as Sonifuran (tradename);

picibanil from Chugai Pharmaceutical Co., Ltd. as Picibanil (tradename); and ubenimex from Nippon Kayaku Co., Ltd. as Bestatin (tradename).

The above-mentioned other anticancer agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from Astra Zeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

In the process according to the invention, preferred therapeutic unit may vary in accordance with, for example, the administration route of the compound of the invention, the type of the compound of the invention used, and the dosage form of the compound of the invention used; the type, administration route and dosage form of the other anticancer agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound of the invention may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other anticancer agent used in combination with the compound of the invention is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 m$^2$; 50 mg in one administration for an area of 1.25 m$^2$ to less than 1.5 m$^2$; 60 mg in one administration for an area of 1.5 m$^2$ or more. This dose is appropriately increased or decreased depending on the condition of the patient.

The therapeutic unit for gemcitabine is, for example, 1 g as gemcitabine/m$^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/m$^2$ (body surface area) or less, and it may be appropriately increased or decreased within the range.

The therapeutic unit for etoposide is such that, for example, in the case of intravenous injection, 60 to 100 mg/m$^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/m$^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/m$^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/m$^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/m² is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/m² is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/m² is administered once a day by intravenous drip infusion for 3 or 4 times at an interval of one week, followed by withdrawal from medication for at least two weeks.

The therapeutic unit for topotecan is such that, for example, 1.5 mg/m² is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/m² is administered on the first day by intravenous drip infusion, and then 250 mg/m² is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m² of 5-FU and 200 mg/m² of leucovorin are administered from the first day to the fifth day by intravenous drip infusion, and this course is repeated at an interval of 4 weeks.

The invention is described more concretely with reference to the following Examples and Production Examples, which, however, are not intended to restrict the scope of the invention.

In thin-layer chromatography in Examples and Production Examples, Silica gel$_{60}$F$_{254}$ (Merck) was used for the plate, and a UV detector was used for detection. Wakogel™ C-300 or C-200(Wako Pure Chemical Industries) or NH (Fuji Silysia Chemical) was used for column silica gel. In MS spectrometry, used was JMS-SX102A (JEOL) or QUATTROII (Micromass). In NMR spectrometry, dimethylsulfoxide was used as the internal standard in a heavy dimethylsulfoxide solution; a spectrometer of Gemini-300 (300 MHz; Varian), VXR-300 (300 MHz; Varian), Mercury 400 (400 MHz; Varian), JNM-AL400(400 MHx; JEOL) or Inova 400(400 MHz; Varian) was used; and all δ values are by ppm.

The XRPD patterns were collected on a BRUKER axs D8 ADVANCE. Copper K-Alpha 1 radiation at 35 kV, 40 mA was used. Samples were scanned between 4 and 40° 2Theta at 0.2°/min. sec/step (step; 0.014, step time; 42.4 s). Intensity of X-ray diffraction was obtained as counts or counts per second in Y-axis. The intensities depend on not only degree of 2 theta but also amounts of a sample, crystallinity of a sample, crystalline form of a sample and salt form of a sample.

The meanings of the abbreviations in Example section are mentioned below.
s: singlet
d: doublet
dd: double doublet
t: triplet
dt: double triplet
q: quartet
m: multiplet
br: broad
J: coupling constant
Hz: hertz
DMSO-d$_6$: heavy dimethylsulfoxide
BH3-DMS: borane-dimethyl sulfide complex
Bu$_4$NHSO$_4$: tetrabutylammonium hydrogensulfate
Hf(OTf)$_4$: hafnium trifluoromethanesulfonate
MTBE: tert-butyl methyl ether

PRODUCTION EXAMPLE 1

Production of 7-chloro-3-(2,6-dichlorophenyl)-4-imino-3,4-dihydropyrimido[4,5-d]pyrimidin-2(1H)-one

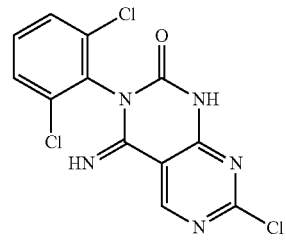 [SMILES: N=c1c2cnc(Cl)nc2[nH]c(=O)n1-c1c(Cl)cccc1Cl]

1.12 g of sodium hydride was added to an N,N-dimethylformamide (35 mL) solution of 3.0 g of 4-amino-2-chloropyrimidine-5-carbonitrile, and stirred at room temperature for 5 minutes. 4.38 g of 2,6-dichlorophenyl isocyanate was added to the reaction liquid, and stirred at room temperature for 1 hour. Ethyl acetate and aqueous 1 N hydrochloric acid solution were added to the reaction solution, and the organic layer was separated. This was washed with saturated saline water, dried with anhydrous magnesium sulfate, and the solvent was evaporated away. The precipitated solid was solidified with a mixed solvent of methanol/ethyl acetate and taken out through filtration to obtain 3.8 g of the entitled compound as a white solid.

$^1$H-NMR (400 MHz, DMSO-$d_6$) δ: 9.33 (1H, s), 7.66 (2H, d, J=8.2 Hz), 7.53 (1H, t, J=8.2 Hz) ESI-MS Found: m/z [M+H] 342

REFERENCE EXAMPLE 1

Production of 2'-methyl-2',3'-dihydro-1'H-spiro[cyclopropane-1,4'-isoquinolin]-7'-amine 1) Production of methyl 1-(2-cyanophenyl)cyclopropanecarboxylate

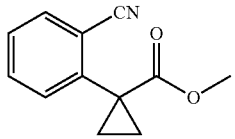

1.5 g of tetra-n-butylammonium bromide, 6.5 g of 1,2-dibromoethane and 20 mL of aqueous 50% sodium hydroxide solution were added to a toluene (40 mL) solution of 4.0 g of methyl 2-cyanophenylacetate, and stirred at room temperature for 1 hour. Water was added to the reaction liquid, and extracted with ethyl acetate. The organic layer was washed with saturated saline water, dried with anhydrous magnesium sulfate, and the solvent was evaporated away under reduced pressure. The crude product was purified through silica gel column chromatography (hexane/ethyl acetate) to obtain 3.0 g of the entitled compound as a colorless compound.

$^1$H-NMR (400 MHz, CDCl$_3$) δ: 7.66 (1H, dd, J=7.6, 1.2 Hz), 7.55 (1H, td, J=7.6, 1.2 Hz), 7.43-7.36 (2H, m), 3.66 (3H, s), 1.82 (2H, q, J=3.7 Hz), 1.30 (2H, q, J=3.7 Hz)

ESI-MS Found: m/z [M+H] 206

2) Production of methyl 1-[2-(aminomethyl)phenyl]cyclopropanecarboxylate monohydrochloride

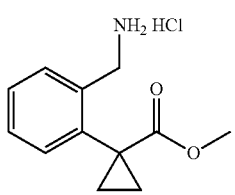

1.6 g of 10% palladium-carbon was added to an ethanol (50 mL) solution of 2.95 g of the compound obtained in the above reaction 1), and stirred in a hydrogen atmosphere under 2 atmospheric pressure at room temperature for 3 hours. The palladium-carbon was removed through filtration, the filtrate was concentrated under reduced pressure, and the crude product was washed with diethyl ether to obtain 3.2 g of the entitled compound as a colorless solid.

$^1$H-NMR (DMSO-$d_6$) δ: 8.47 (2H, s), 7.55 (1H, d, J=6.8 Hz), 7.38 (3H, td, J=7.2, 2.1 Hz), 7.36-7.29 (2H, m), 4.04 (2H, d, J=4.9 Hz), 3.54 (3H, s), 1.61-1.56 (2H, m), 1.33-1.29 (2H, m)

ESI-MS Found: m/z [M+H] 206

3) Production of 1',2'-dihydro-3'H-spiro[cyclopropane-1,4'-isoquinolin]-3'-one

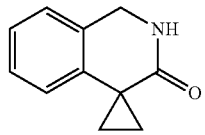 [SMILES: O=C1NCc2ccccc2C12CC2]

4 mL of aqueous 5 N sodium hydroxide solution was added to a methanol (50 mL) solution of 3.2 g of the compound obtained in the above reaction 2), and stirred at room temperature for 30 minutes. This was neutralized with aqueous 1 N hydrochloric acid added thereto, and methanol was evaporated away under reduced pressure. The residue was diluted with water, and extracted three times with ethyl acetate. The organic layer was washed with saturated saline water, dried with anhydrous magnesium sulfate, and the solvent was evaporated away under reduced pressure to obtain 2.1 g of the entitled compound as a colorless solid.

$^1$H-NMR (CDCl$_3$) δ: 7.23 (1H, td, J=7.8, 1.1 Hz), 7.18 (1H, td, J=7.3, 1.1 Hz), 7.10 (1H, dd, J=7.3, 1.0 Hz), 6.73 (1H, dd, J=7.8, 1.0 Hz), 4.69 (2H, d, J=1.5 Hz), 1.85 (2H, q, J=3.7 Hz), 1.24 (2H, q, J=3.7 Hz)

ESI-MS Found: m/z [M+H] 174

4) Production of 7'-nitro-1',2'-dihydro-3'H-soiro[cyclopropane-1,4'-isoquinolin]-3'-one

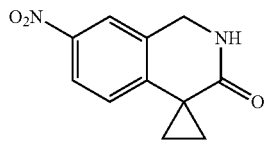 [SMILES: O=C1NCc2cc([N+](=O)[O-])ccc2C12CC2]

1.3 g of potassium nitrate was gradually added to a sulfuric acid (60 mL) solution of 2.1 g of the compound obtained in the above reaction 3), taking 5 minutes, and further stirred at room temperature for 10 minutes. The reaction liquid was poured into ice water, the precipitated crystal was taken out through filtration, and washed with water to obtain 2.4 g of the entitled compound as a yellow solid.

$^1$H-NMR (CDCl$_3$) δ: 8.09 (1H, dd, J=8.8, 2.4 Hz), 8.01 (1H, t, J=2.4 Hz), 6.86 (1H, d, J=8.8 Hz), 6.30 (1H, s), 4.78 (2H, d, J=1.5 Hz), 2.01 (2H, q, J=4.1 Hz), 1.35 (2H, q, J=4.1 Hz)

ESI-MS Found: m/z [M+H] 219

5) Production of 7'-nitro-1',2'-dihydro-3'H-spiro[cyclopropane-1,4'-isoquinoline]

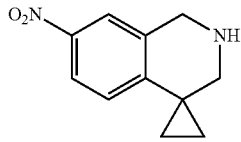 [SMILES: O=[N+]([O-])c1ccc2c(c1)CNCC21CC1]

With cooling with ice, 6.3 g of boron trifluoride-diethyl ether complex was added to a tetrahydrofuran suspension of 1.3 g of sodium borohydride, and stirred for 1 hour. A tetrahydrofuran (100 ml) solution of 2.4 g of the compound obtained in the above reaction 4) was added to the reaction liquid, and heated under reflux for 2 hours. The reaction liquid was cooled, and then neutralized with aqueous saturated sodium bicarbonate solution. The solvent was evaporated away under reduced pressure, the residue was dissolved in ethanol, 5 N hydrochloric acid was added to it, and heated under reflux for 1 hour. The reaction liquid was cooled, then the solvent was evaporated away under reduced pressure, and the residue was neutralized with aqueous potassium carbonate solution. The aqueous layer was extracted with chloroform, the organic layer was dried with anhydrous magnesium sulfate, and the solvent was evaporated away under reduced pressure to obtain the entitled compound.

ESI-MS Found: m/z [M+H] 205

6) Production of 2'-methyl-7'-nitro-2',3'-dihydro-1'H-spiro[cyclopropane-1,4'-isoquinoline]

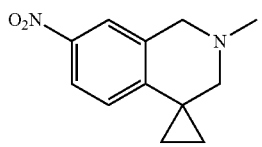 [SMILES: CN1Cc2cc([N+](=O)[O-])ccc2C2(CC2)C1]

1.5 g of sodium cyanoborohydride was added to a methanol (50 mL) solution of the compound (2.3 g) obtained in the above reaction 5), 2.7 mL of aqueous 37% formaldehyde solution and 0.7 mL of acetic acid, and stirred at room temperature for 15 hours. The reaction liquid was neutralized with aqueous saturated sodium bicarbonate solution, and methanol was evaporated away under reduced pressure. The residue was diluted with water and extracted three times with chloroform. The organic layer was dried with anhydrous magnesium sulfate, the solvent was evaporated away under reduced pressure, and the crude product was purified through silica gel column chromatography (hexane/ethyl acetate) to obtain 1.7 g of the entitled compound as a colorless solid.

$^1$H-NMR (CDCl$_3$) δ: 7.97 (1H, dd, J=8.8, 2.4 Hz), 7.91 (1H, d, J=2.4 Hz), 6.78 (1H, d, J=8.8 Hz), 3.77 (2H, s), 2.57 (2H, s), 2.48 (3H, s), 1.16-1.12 (2H, m), 1.10-1.06 (2H, m)

ESI-MS Found: m/z [M+H] 219

7) Production of 2'-methyl-2',3'-dihydro-1'H-spiro[cyclopropane-1,4'-isoquinolin]-7'-amine

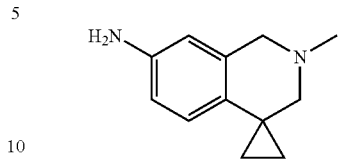

800 mg of 10% palladium-carbon was added to an ethanol (20 mL) solution of 1.7 g of the compound obtained in the above reaction 6), and stirred in a hydrogen atmosphere under 1 atmospheric pressure at room temperature for 15 hours. Palladium-carbon was removed through filtration, the filtrate was concentrated under reduced pressure, and the crude product was purified through basic silica gel column chromatography (hexane/ethyl acetate) to obtain 1.1 g of the entitled compound as a colorless solid.

$^1$H-NMR (CDCl$_3$) δ: 6.50-6.48 (2H, m), 6.38-6.36 (1H, m), 3.61 (2H, s), 3.50 (2H, s), 2.49 (2H, s), 2.42 (3H, s), 0.91 (2H, dd, J=6.3, 4.6 Hz), 0.81 (2H, dd, J=6.3, 4.6 Hz)

ESI-MS Found: m/z [M+H] 189

REFERENCE EXAMPLE 2

Production of 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one dihydrochloride

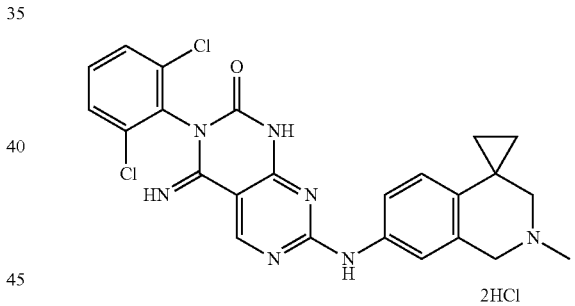

A 1-butanol solution of 1.5 g of 7-chloro-3-(2,6-dichlorophenyl)-4-imino-3,4-dihydropyrimido[4,5-d]pyrimidin-2 (1H)-one obtained in Production Example 1, 1 g of 2'-methyl-2',3'-dihydro-1'H-spiro[cyclopropane-1,4'-isoquinolin]-7-amine obtained in Reference Example 1, and 0.83 g of p-toluenesulfonic acid monohydrate was stirred at 90° C. for 15 minutes. The reaction liquid was cooled, then diluted with chloroform, and the organic layer was washed with aqueous saturated sodium bicarbonate solution and then saturated saline water, and dried with anhydrous magnesium sulfate, filtered, and the solvent was evaporated away. Thus obtained, the roughly-purified product was purified through basic silica gel column chromatography to obtain 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one. This was dissolved in a mixed solvent of chloroform/methanol, and 1.5 equivalents of aqueous hydrochloric acid solution was added thereto, and stirred at room temperature for 5 minutes. Then, the solvent was evaporated away, and the residue was washed with ethyl acetate to obtain 1.5 g (yield, 64%) of the entitled compound as a yellow solid.

$^1$H-NMR (400 MHz, DMSO-d$_6$) δ: 11.83 (1H, brs), 10.05 (1H, brs), 9.10 (1H, s), 8.88 (1H, s), 7.79-7.68 (1H, m), 7.63-7.59 (2H, m), 7.47 (1H, t, J=8.2 Hz), 7.38 (1H, d, J=8.3 Hz), 6.63 (1H, d, J=8.5 Hz), 3.59 (2H, s), 2.44 (2H, s), 2.32 (3H, s), 0.90-0.81 (4H, m)

ESI-MS Found: m/z [M+H]$^+$ 494

EXAMPLE 1

Production of 2'-methyl-2',3'-dihydro-1'H-spiro[cyclopropane-1,4'-isoquinolin]-7'-amine dihydrochloride 1) Production of 2'-methyl-1'H-spiro[cyclopropane-1,4'-isoquinoline]-1',3'(2'H)-dione

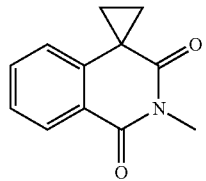

To a solution of N-methylhomophthalimide (4.05 kg), 1,2-dibromoethane (2.39 L), and Bu$_4$NHSO$_4$ (785 g) in N,N-dimethylformamide (32 L) were added K$_2$CO$_3$ (6.39 kg) and N,N-dimethylformamide (8.5 L) at room temperature. Then the solution was heated to 70° C., and was stirred for 2 hours at 68~70° C. After cooling the reaction mixture to 40° C., water (81 L) was added. After the slurry was stirred for 1 hour at 40° C., it was allowed to cool to room temperature and was stirred overnight. The suspension was filtered, and the obtained wet crystal was washed with the mixture of N,N-dimethylformamide and water (N,N-dimethylformamide: water=1:1, 20 L), twice, and water (20 L), sequentially. It was dried at room temperature under N2 flow for several hours and then under the reduced pressure overnight to afford the title compound as pale pink crystal (4.67 kg, 4.30 kg assay, 92% yield).

$^1$H-NMR (400 MHz, CDCl$_3$) δ: 8.26 (1H, dd, J=7.9, 0.9 Hz), 7.59-7.54 (1H, m), 7.41-7.35 (1H, m), 6.81 (1H, d, J=8.1 Hz), 3.41 (3H, s), 2.14 (2H, dd, J=7.9, 4.0 Hz), 1.63 (2H, dd, J=7.9, 4.0 Hz).

2) Production of 2'-methyl-7'-nitro-1'H-spiro[cyclopropane-1,4'-isoquinoline]-1',3'(2'H)-dione

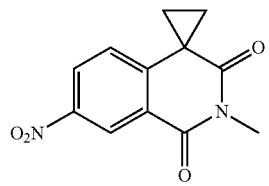 [SMILES: CN1C(=O)c2cc([N+](=O)[O-])ccc2C2(CC2)C1=O]

To the cooled mixture of H$_2$SO$_4$ (9.80 L) and HNO$_3$ (4.90 L) was added the compound prepared by the procedure 1) (4.65 kg) at 0~5° C. over 2 hours. The obtained slurry was stirred for 1 hour at 0~5° C. The mixture was diluted with acetic acid (19 L) below 10° C. Then the obtained solution was poured into cooled water (90 L) over 1 hour. Acetic acid (5.5 L) and water (8 L) was used for rinse. The obtained yellow suspension was stirred overnight at 10° C. After the suspension was filtered, the obtained wet crystal was washed with water (25 L), twice. It was dried at room temperature under N2 flow for 3.5 h, then under reduced pressure overnight to afford the crude compound as pale yellow crystal (6.57 kg, 4.93 kg assay, 94% yield). The crude crystal was suspended in the MTBE (62 L) and it was stirred overnight at room temperature. After it was filtered, the obtained wet crystal was washed with MTBE (24 L, 12 L), twice. It was dried at room temperature under N2 flow for 1 h, then under reduced pressure overnight to afford the title compound as pale yellow crystal (4.76 kg, 4.52 kg assay, 92% recovered).

$^1$H-NMR (400 MHz, CDCl$_3$) δ: 9.11 (1H, d, J=2.4 Hz), 8.39 (1H, dd, J=8.8, 2.4 Hz), 6.98 (1H, d, J=8.8 Hz), 3.44 (3H, s), 2.32 (2H, dd, J=8.2, 4.2 Hz), 1.77 (2H, dd, J=8.2, 4.2 Hz).

3) Production of 2'-methyl-7'-nitro-2',3'-dihydro-1'H-spiro[cyclopropane-1,4'-isoquinoline]hydrochloride

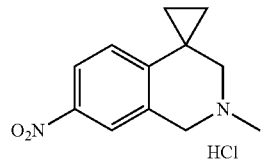 [SMILES: CN1Cc2cc([N+](=O)[O-])ccc2C2(CC2)C1 ; Cl]

The compound prepared by the procedure 2) (4003 g) was suspended in tetrahydrofuran (28 L) and the mixture was warmed to 60° C. BH3-DMS (6.39 L) was dropwisely added at the same temperature over 2 hours. The reaction mixture was stirred at 57-62° C. for 24 h, and then at 60-65° C. for 24 hours under N2 flow. Tetrahydrofuran (2.43 L) was added after 20 h, because of the decrease of the amount of solvent. After the solution was cooled to 10° C., ethanol (24 L) was slowly added. It was further stirred for 1 hour. The solution was then heated to remove tetrahydrofuran with the bath temperature controlled from 80 to 100° C. Temperature of the solution was finally reached to 75° C. After tetrahydrofuran was almost removed, 3 M HCl (40 L) was added and the solution was heated to 78° C. for 2 hours. After the solution was cooled to 10° C., 5M NaOH (32 L) and dichloromethane (40 L) was added with cooling (<15° C.) and the organic phase was separated. After the water phase was extracted with dichloromethane (60 L), it was filtered to remove the insoluble materials and was re-extracted with dichloromethane (20 L). The combined organic phase was concentrated to 30 L. The solvent was switched to toluene and its volume was reduced to 20 L. To the solution, toluene (60 L) and activated charcoal (400 g) were added, and it was stirred overnight. After filtration, it was washed with toluene (12 L), twice. The water phase remained in the toluene solution was separated off and the organic phase was dried through sodium sulfate (2 kg). After filtration, the dring agent was washed with toluene (5 L), twice. 4M HCl-Dioxane (3.75 L) was portionwisely added to the combined solution at room temperature and it was stirred overnight. The suspension was filtered. The obtained crystal was washed twice with toluene (20 L) and was dried under vacuum for one day to afford the title product (3.19 kg, 2.27 kg assay of free aniline, 64.0% yield).

¹H-NMR of free base (400 MHz, CDCl₃) δ: 7.97 (1H, dd, J=8.8, 2.4 Hz), 7.91 (1H, d, J=2.4 Hz), 6.78 (1H, d, J=8.8 Hz), 3.77 (2H, s), 2.56 (2H, s), 2.48 (3H, s), 1.17-1.11 (2H, m), 1.10-1.05 (2H, m).

4) Production of 2'-methyl-2',3'-dihydro-1'H-spiro[cyclopropane-1,4'-isoquinolin]-7'-amine dihydrochloride

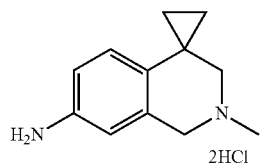

To a solution of the compound prepared by the procedure 3) (5.9 kg, 4.0 kg as free) in ethanol (20 L) was added zinc powder (4.79 kg) at 70° C. over 10 minutes, and then 12M HCl (10.69 L) in ethanol (12 L) over 60 minutes at 70~78° C. The obtained yellow suspension was stirred for 1 hour at 70° C. After cooling to 5° C., dichloromethane (53.24 kg) and 5M NaOH (37.74 kg) was added. It was stirred for 1 hour at room temperature and then filtered through Celite. The wet cake was washed with the mixture of water and dichloromethane (1:1, 20 L), twice. The filtrate and washings were combined and the phases were separated. The aqueous layer was extracted with dichloromethane (53.05 kg, 26.63 kg), twice. The combined organic layer was washed with 1M NaOH (20 L) and water (20 L). The obtained organic layer was evaporated and the solvent was switched to 2-propanol. The volume was adjusted to 40 L. Then the solution was treated with activated carbon (400 g) for 40 minutes at room temperature. The suspension was filtered and the wet carbon was washed with 2-propanol (20 L), twice. To the combined filtrate and washings were added 2M HCl in ethanol (18.3 L) over 60 minutes at room temperature and it was stirred overnight. The suspension was filtered and the wet crystal was washed with 2-propanol (12 L), twice. It was dried at room temperature under N2 flow for several hours, then under reduced pressure overnight to afford the title compound as pale yellow crystal (6.35 kg, 3.83 kg assay of free aniline, quantitative yield).

¹H-NMR of free base (400 MHz, CDCl₃) δ: 6.50-6.48 (2H, m), 6.38-6.36 (1H, m), 3.61 (2H, s), 3.50 (2H, s), 2.49 (2H, s), 2.42 (3H, s), 0.91 (2H, dd, J=6.3, 4.6 Hz), 0.81 (2H, dd, J=6.3, 4.6 Hz).

ESI-MS Found: M/Z [M+H] 189

EXAMPLE 2

Production of 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one dihydrochloride 3.5 hydrate To a stirred suspension of 2'-methyl-2',3'-dihydro-1'H-spiro[cyclopropane-1,4'-isoquinolin]-7'-amine dihydrochloride (1.90 kg, 7.27 mol, 1.09 eq.) in chloroform (19 L) at room temperature was added 5 N NaOH (3.8 L), and the mixture was stirred for 5 minutes. The chloroform layer was separated and the aqueous layer was extracted with chloroform (9.5 L). Combined chloroform layers were washed with 5% aqueous NaCl (9.5 L), then dried over anhydrous sodium sulfate (3.8 kg) for 1 hour. Sodium sulfate was filtered and washed with chloroform (3.8 L). Combined filtrate and washing were evaporated to give crude oil. Methanol (4.6 L) was added and the solution was evaporated to give 2'-methyl-2',3'-dihydro-1'H-spiro[cyclopropane-1,4'-isoquinolin]-7'-amine (1.40 kg) as brownish crystals in crude 102% recovery.

To a stirred solution of the compound obtained above (1.40 kg, 7.27 mol, 1.09 eq.) in methanol (10 L) were added 4 N HCl-ethyl acetate (1.92 L) below 15° C. and then Hf(OTf)₄ (103 g) was added. After cooled to 14° C., 7-chloro-3-(2,6-dichlorophenyl)-4-imino-3,4-dihydropyrimido[4,5-d]pyrimidin-2(1H)-one (2.28 kg, 6.66 mol) and methanol (1.5 L) were added and the slurry was stirred at room temperature for 5 hours. Methanol (6.9 L) and ethyl acetate (9.2 L) were added and the slurry was stirred at room temperature for 1 hour. Ethyl acetate (4.6 L) was added and the slurry was stirred for 1 hour. Then, ethyl acetate (4.6 L) was added and the slurry was stirred at room temperature overnight. The slurry was filtered, washed with methanol-ethyl acetate (1:1, 6.9 L) and then methanol-ethyl acetate (1:2, 6.9 L), and dried at room temperature by sucking under N2 flow for 6 hours. then under reduced pressure with N2 flow overnight to give the crude 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H-one dihydrochloride (3.883 kg, 3.324 kg assay of free base) as yellow crystals in 101% yield.

To a stirred suspension of the crude compound obtained above (3.862 kg, 3.306 kg assay of free base, 6.687 mol) in chloroform (79 L) and methanol (33 L) at room temperature was added 5% aqueous NaHCO₃ (33 L), and the mixture was stirred for a few minutes. Organic layer was separated and dried over anhydrous sodium sulfate (6.62 kg). Sodium sulfate was removed by filtration and washed with chloroform-methanol (12:5, 14.1 L). The filtrate and washing were concentrated to 6 L and ethanol (33 L) was added and the solution was concentrated to 10 L. Ethanol (33 L) was added again and the solution was concentrated to 10 L. Ethanol (16.5 L) and N,N-dimethylformamide (6.6 L) were added to the slurry and heated to 55° C. 2N HCl-ethanol (3.34 L) was added at 55° C., then 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one dihydrochloride 3.5 hydrate (17 g) was added and 2N HCl-ethanol (3.68 L) was added dropwise over 1 hour at 55° C. and aged for 1 hour at the same temperature. Then the slurry was cooled gradually to room temperature and aged for overnight at room temperature. The slurry was filtered, washed with ethanol (9.9 L×2 times), and dried at the room temperature under N2 flow for several hours then under reduced pressure overnight. The dried crystal was treated with wet N2 to control water content in the crystal. 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one dihydrochloride 3.5 hydrate (3.401 kg, 2.600 kg assay of free base) was obtained as pale yellow crystals in 79% yield. ¹H-NMR (400 MHz, DMSO-d₆) δ: 11.83 (1H, brs), 10.05 (1H, brs), 9.10 (1H, s), 8.88 (1H, s), 7.79-7.68 (1H, m), 7.63-7.59 (2H, m), 7.47 (1H, t, J=8.2 Hz), 7.38 (1H, d, J=8.3 Hz), 6.63 (1H, d, J=8.5 Hz), 3.59 (2H, s), 2.44 (2H, s), 2.32 (3H, s), 0.90-0.81 (4H, m).

ESI-MS Found: m/z [M+H] 494

XRPD Patterns:
(2 theta(degrees), Intensity(cps)): (8.4°, 26.4), (12.7°, 20.4), (15.3°, 18.8), (16.3°, 18.1), (22.32°, 30.9), (24.5°, 24.5), (24.9°, 31.2), (26.5°, 24.6), (28.6°, 16.6).

Water Content:

When water content of the crystalline was measured by Karl Fischer test using a Kyoto electronics manufacturing MKC-510, the water content of the crystalline was 10.3%, theoretically 10.0%.

Industrial Applicability

The compounds of the invention have excellent Weel kinase-inhibitory effect and are therefore useful in the field of medicines, especially treatment of various cancers.

What is claimed is:

1. A crystalline form of a 3.5 hydrate of Compound A dihydrochloride:

Compound A

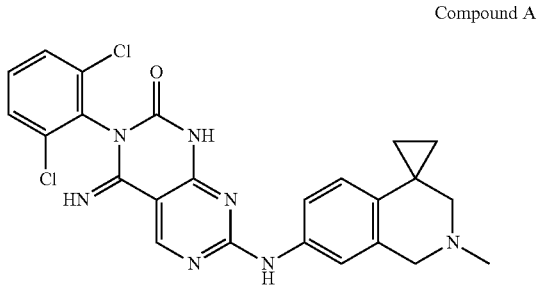 [SMILES: CN1Cc2cc(Nc3ncc4c(=N)n(-c5c(Cl)cccc5Cl)c(=O)[nH]c4n3)ccc2C2(CC2)C1]

having an X-ray powder diffraction pattern, obtained using Cu K alpha radiation, containing the following angle 2 theta values: 8.4°, 22.3° and 24.9°, and at least one angle 2 theta value selected from the group consisting of: 12.7°, 15.3°, 16.3°, 24.4°, 26.5°, and 28.6°.

2. A process for preparing a crystalline form of a 3.5 hydrate of Compound A dihydrochloride, which comprises the steps of:

(a) concentrating a solution of Compound A in an organic solvent to form a slurry;

(b) treating the slurry of step (a) with hydrogen chloride in a solvent on heating;

(c) cooling the slurry of step (b) to room temperature;

(d) collecting crystals from the resulting slurry of step (c);

(e) drying the crystals of step (d); and (f) treating the dried crystals of step (e) with wet inert gas to stabilize water content in the desired crystalline form.

3. A pharmaceutical composition comprising a therapeutically-effective amount of the crystalline hydrate compound of claim 1, and a pharmaceutically acceptable carrier or diluent.

4. A process for preparing a compound of formula (6):

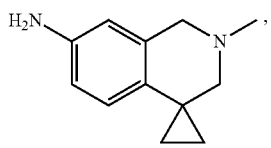 (6)

or a salt thereof, which comprises the steps of:

(a) reacting a compound of formula (1):

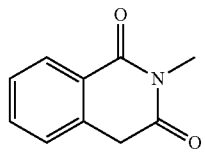 (1)

with a compound of formula (2):

$X^1$—$CH_2CH_2$—$X^2$ (2)

wherein $X_1$ and $X^2$ each independently is a leaving group, to obtain a compound of formula (3):

 (3)

(b) nitrating a compound of formula (3) to obtain a compound of formula (4):

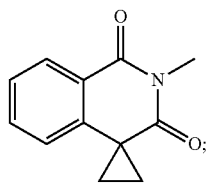 (4)

(c) reducing oxo groups of the compound of formula (4) to obtain a compound of formula (5):

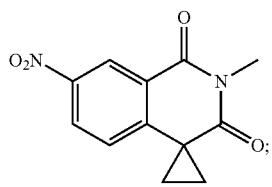 (5)

or a salt thereof;

(d) reducing a nitro group of the compound of formula (5) or a salt thereof to obtain a compound of formula (6) or a salt thereof; and optionally converting said compound of formula (6) into a salt thereof.

5. The hydrate of claim 1, having an X-ray powder diffraction pattern, obtained using Cu K alpha radiation, containing the following angle 2 theta values: 8.4°, 22.3°, 24.9° and 12.7°.

6. The process of claim 2, wherein the crystalline form has an X-ray powder diffraction pattern, obtained using Cu K alpha radiation, containing the following angle 2 theta values: 8.4°, 22.3° and 24.9°, and at least one angle 2 theta value selected from the group consisting of: 12.7°, 15.3°, 16.3°, 24.4°, 26.5°, and 28.6°.

7. The process of claim 2, wherein the organic solvent of step (a) is an alcohol-containing solvent or a mixture thereof.

8. The process of claim 7, wherein the alcohol-containing solvent is selected from the group consisting of methanol, ethanol, propanol, and isopropanol.

9. The process of claim 7, wherein the organic solvent of step (a) optionally contains organic or inorganic solvents other than alcohol.

10. The process of claim 9, wherein the organic or inorganic solvents are selected from the group consisting of chloroform, dichloromethane, N, N-dimethylformamide, and water.

\* \* \* \* \*